United States Patent [19]

Barber

[11] 4,399,813

[45] Aug. 23, 1983

[54] APPARATUS AND METHOD FOR REMOVING A PROSTHESIS EMBEDDED IN SKELETAL BONE

[76] Inventor: Forest C. Barber, P.O. Box 7744, Fort Worth, Tex. 76111

[21] Appl. No.: 227,389

[22] Filed: Jan. 22, 1981

[51] Int. Cl.³ .............................................. A61F 5/04
[52] U.S. Cl. ............................ 128/92 EC; 128/92 EB
[58] Field of Search ........... 128/92 R, 92 EB, 92 EC, 128/92 ED

[56] References Cited

U.S. PATENT DOCUMENTS 2,638,092  5/1953  Dorr .................................. 128/92 R
4,237,875  12/1980  Termanini ...................... 128/92 BA

FOREIGN PATENT DOCUMENTS

735333  5/1943  Fed. Rep. of Germany ... 128/92 EC
197710  10/1977  U.S.S.R. .......................... 128/92 EC Primary Examiner—Kyle L. Howell
Assistant Examiner—C. W. Shedd
Attorney, Agent, or Firm—Peter J. Murphy

[57] ABSTRACT

A drill assembly includes a handle carrying a mount for a pneumatic drill motor, and an elongated tubular support enclosing an extended motor shaft which carries a drill bit chuck projecting from the end of that support. The drill assembly coacts with a drill guide assembly including an elongated tubular guide for receiving the tubular support in sliding relation, and having a rotary bearing at its lower end for rotationally supporting the drill bit. The lower end face is concave to enable seating on the prosthesis tip to be drilled. The drill guide assembly includes an offset handle and a stop clamp and depth gauge for coaction with the drill assembly handle to control the depth of drilling. An extractor assembly, for coaction with an undercut drilled hole in the prosthesis, includes an extractor having an externally threaded body and a tubular internally threaded T handle for that body. The body includes an axial shaft to be received in the hole with a lateral toe at the distal end defining a ledge. The extractor further includes an elongated cam slot for guiding a follower wedge, which wedge is moved axially relative to the extractor by the end of the tubular holder to effect lateral displacement of the shaft to place the toe within the undercut recess of the hole. A slide hammer, coupled to the extractor holder, imparts axial blows to the assembly to extract the prosthesis tip.

22 Claims, 17 Drawing Figures

APPARATUS AND METHOD FOR REMOVING A PROSTHESIS EMBEDDED IN SKELETAL BONE

This invention relates to the extraction of an earlier implanted metallic prosthesis from skeleton bone, and more particularly to the extraction of the distal tip portion of an elongated prosthesis which remains securely embedded in the bone after fracture of the prosthesis and removal of the relatively free proximal portion of that prosthesis.

Possibly as the result of an accident or a war injury, or the crippling effects of bone disease, it is sometimes desirable to replace a joint of the human body with an artificial joint. The total replacement of joints, and the consequent possibility of a future revision of a surgically implanted joint, is a relatively new field of surgery. Its development is being enhanced by the discovery, and application in the surgery field, of newer and stronger metals and of new plastics and similar materials. For example, a total hip replacement consists of replacing the existing acetabular cup with a high polymer polyethylene plastic cup, and replacing the rounded head of the femur with a metal prosthesis including a proximal ball which coacts with the plastic cup and an elongated stem which is extended into and embedded in the intramedullary canal of the femoral shaft. Even though this metal femoral component of the prosthesis is constructed of extremely hard metal, because of all of the stress and strain that is placed upon it by the action of the human body in the performance of its daily routine, it sometimes happens that the shaft of the prosthesis will fracture; and replacement of the entire femoral component will then be necessary in order to allow the wearer to remain ambulatory without experiencing considerable pain. The difficulty of extracting the tip portion of a fractured prosthesis stem is readily apparent when one considers that this tip portion is implanted possibly deep within the intramedullary canal of the bone and possibly embedded within surgical cement, and that the surgical area is confined considering the narrow siz of the bone shaft.

This invention then is concerned with the total replacement of joints in the human body; and is particularly concerned with the aspect of revision surgery which involves the removal of an earlier implanted prosthesis which has fractured, in order to enable implantation of a replacement prosthesis. While the invention is concerned broadly with joint replacement in the human body, and possibly with other procedures involving prosthesis implants, the invention will be described with particular reference to a total hip replacement.

One approach which has been used in the past to remove the embedded tip of the femoral stem of a hip joint prosthesis involves the removal of the surgical cement from the annular space between the stem and the femoral cortex. Tools for this procedure may include osteotomes or power instruments. Because this annular space is usually very narrow, it may be difficult to remove the cement around the broken stem for a distance sufficient to allow it to be dislodged. Moreover, because of this confined space, a frequent complication of this procedure is the perforation of the cortex. This complication may require bone grafting and the use of a long-stem femoral component for the revision implant. The use of such long stem femoral component further compounds the complication, since the achieving of excellent cement distribution and pressurization is much more difficult with the use of such long-stem component, especially if there is a hole in the femur. In addition, the future surgical revision of the long-stem femoral component, should it fail, increases the technical difficulties.

Another known approach for the removal of the embedded tip of a prosthesis stem involves creating a window in the cortex of the femur to enable the driving of the stem toward the cut surface of the femoral neck through the use of a driving tool such as a carbide chisel. One complication of this procedure is that the creating of the window in the femur produces a stress riser which weakens the femur and predisposes this area to fracture. To overcome the resulting femoral weakness, it is necessary to use a long-stem component for the replacement prosthesis, in order to bypass the stress riser. Complications accompanying the long-stem component have been discussed above. Accessory fixation and/or bone grafting may also be required. With this approach, a possible mechanical problem may result from the use of extremely hard so-called space-age metals in the fabrication of the original prosthesis. With such metals it is sometimes difficult, even with a carbide tip chisel, for example, to penetrate the surface of the prosthesis sufficiently to enble it to be driven by the chisel.

The concept of drilling into the fractured proximal end of the embedded prosthesis tip and locking into that drilled hole with some form of extractor device to enable withdrawing of the prosthesis tip, without resorting to either of the above described techniques or approaches, is attractive. One known technique, embodying this concept, involves drilling into the distal end of the stem and utilizing a screw threadedly engaged within the drilled hole as an extractor. While this techique may be useful where the prosthesis has been fabricated from stainless steel or other material having the equivalent or lesser hardness, this technique is not suited for use with prostheses constructed of the harder space-age metals and alloys.

A principal object of this invention is to provide a novel apparatus and method for removal of a prosthesis embedded in a bone shaft, without the necessity or possibility of perforating the bone cortex.

Another object of this invention is to provide a novel apparatus and method for such prosthesis removal where the originally implanted prosthesis has been fabricated from extremely hard metal.

A further object of this invention is to provide a novel apparatus and method for such prosthesis removal by forming a recess in the proximal end of the embedded prosthesis, and engaging that recess with a suitable extraction tool to withdraw the prosthesis from the bone shaft.

Still another object of this invention is to provide a novel apparatus and method for such prosthesis removal which minimizes the complications in connection with the revision surgery.

These objects are accomplished in a method which includes, broadly, the following steps. A bore hole is formed in one end of the prostheses, aligned generally axially with the long dimension of the prosthesis. An undercut ledge is formed in one wall of the hole, spaced from the entrance thereof. The axial shaft of an extractor is inserted into the hole, the shaft having a lateral projection at its distal end providing a transverse ledge. The extractor shaft is displaced laterally within the hole to place its transverse ledge in interfering relation with the undercut ledge. Impact blows are imparted to the extractor shaft along its axis for transmission to the prosthesis through the interfering ledges.

Apparatus for accomplishing these objects includes broadly the following assembly. A drill guide subassembly includes a tubular drill guide, handle means at one end of the drill guide, and the other end of the drill guide provided with a concave end face to overlie and engage the exposed end of the prosthesis. A rotary bearing is provided at said other end of the drill guide for rotationally supporting an end cutting bit projecting therefrom. A drill subassembly includes a tubular support to be slidably received within the tubular drill guide, a drill motor mounted at one end of the tubular support having a drive shaft extending through the support with drill bit chuck means mounted at the projecting end of the shaft. An end cutting bit for drilling an axial hole is mounted in the chuck means and rotationally guided in the bearing means of the drill guide assembly. The drill subassembly, used independently of the drill guide subassembly, cuts an undercut ledge in the axial hole with an appropriate cutting bit. An extractor assembly includes an extractor having an externally threaded body and an internally threaded tubular holder for the body. The extractor has an axial extractor shaft to be received in the hole, the shaft having lateral projection means at its distal end defining a ledge. The extractor has a longitudinal cam slot for guiding a follower wedge, the follower wedge being movable axially by the end face of the holder to move the shaft laterally within the hole to place the ledges in interfering relation. The extractor assembly further includes means coupled to the tubular holder to impart axial impact blows to the extractor.

The novel features and the advantages of the invention, as well as additional objects thereof, will be understood more fully from the following description when read in connection with the accompanying drawings.

DESCRIPTION OF THE PREFERRED EMBODIMENT

Figure 1:
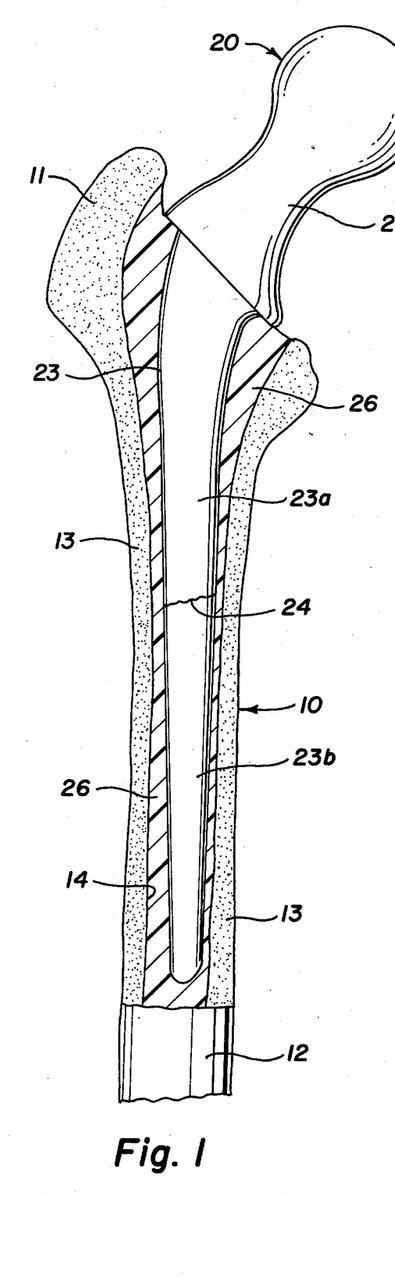
FIG. 1 is a sectional view of the upper end of a femur with the fractured femoral component of a total hip replacement in place.

As background for the following description of the apparatus and method of the invention, FIG. 1 illustrates the upper portion of a human femur along with the femoral component of a total hip replacement. The illustrated femur may be the femur of the right leg as viewed from the front. Referring to FIG. 1, the illustrated portion of a femur 10 includes a portion of the upper enlarged head 11 and a portion of the stem 12. The portion of the head 11 which forms the ball portion of the hip joint has been removed and is replaced by a portion of the implanted prosthesis which is the femoral component 20. This femoral component is formed from a suitable metal, and includes an enlarged spherical ball portion 21 which forms the ball portion of the hip replacement joint, a neck portion 22 which spaces the ball from the head 11 of the femur, and an elongated stem 23 extending from the neck to be embedded within the femur stem. The prosthesis stem 23 has been implanted within the intramedullary canal 14 of the femur, and the annular space between the prosthesis stem and the cortex 13 of the femur has been filled with surgical cement 26 to provide for secure embeddment of the prosthesis within the bone.

To illustrate the problem to which the present invention is directed, FIG. 1 illustrates a fracture 24 of the prosthesis stem 23 within the femur, and without fracture of the femur itself; with a distal end portion of the prosthesis stem 23a remaining integral with the neck and head, and with the distal portion 23b of the prosthesis stem being embedded deep within the intramedullary canal. While a fracture of the prosthesis stem may occur at any point from a point near the neck portion 22 to a point very close to the proximal end, this separated proximal portion 23b will be referred to as the "tip" of the prosthesis or of the femoral component even though this tip may have substantial strength.

For revision surgery following a fracture of the type illustrated in FIG. 1, the femur is preferably displaced from the hip bone sufficiently to allow generally axial access to the intramedullary canal. The proximal portion of the femoral component 20, including the proximal stem portion 23a, has probably become sufficiently loosened from the embedding surgical cement, as a result of the fracture, to allow ready removal from the femur. As background for the detailed descriptions of the apparatus and method of the invention which follow, the method of the invention includes, very broadly, the following steps: (1) removal of the surgical cement which had surrounded the removed prosthesis stem 23a to provide an enlarged access canal to the embedded tip 23b; (2) forming a hole in the exposed proximal end of the embedded tip 23b which is generally aligned with the access canal and the longitudinal axis of the prosthesis tip, and forming a lateral undercut within that hole; (3) engaging the prosthesis tip with an extractor tool having an axial shaft to enter the hole and having a laterally projecting toe to be received in the undercut of that hole, and locking the toe of the extractor tool within the undercut; and (4) exerting a suitable axial force on the extractor tool to dislodge the prosthesis tip from the hold of the femur shaft and/or the surgical cement.

Figure 10:
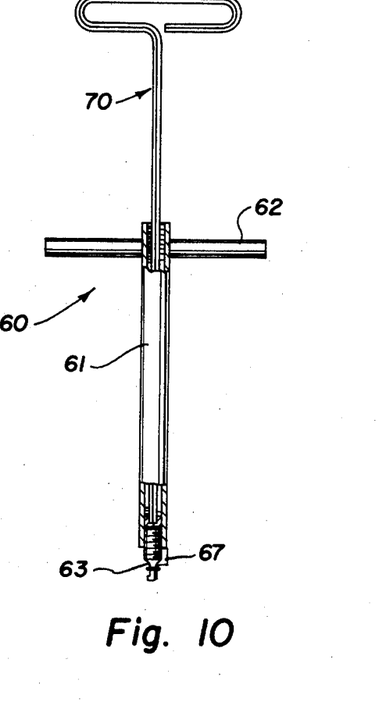
FIG. 10 is a side view of a portion of the extractor assembly including extractor, T handle, and hex wrench.
Figures 11, 12:
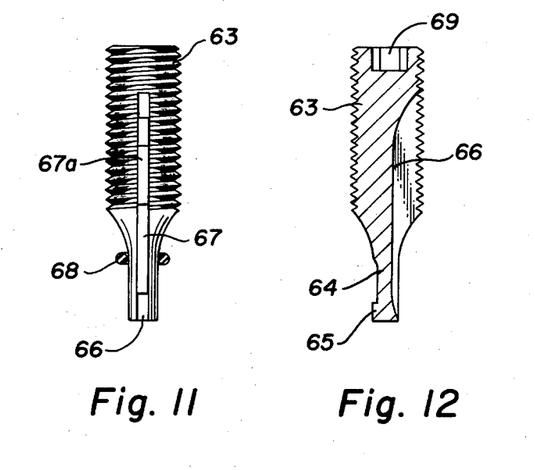
FIGS. 11, 12 and 13 are detail views of the extractor.
Figure 13:
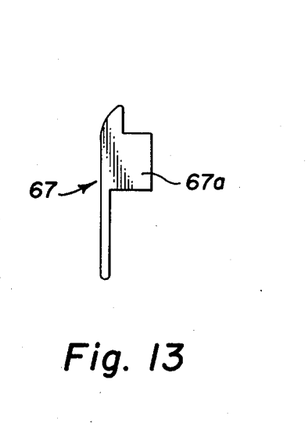

The apparatus of the invention is conveniently described as consisting of three separate assemblies, namely: (1) a drill guide assembly; (2) a drill assembly; and (3) an extractor assembly. The drill guide assembly and the drill assembly are shown in coacting relation in FIG. 2. The drill assembly is shown in additional detail in FIGS. 3 and 8. The components of the extractor assembly are best shown, broadly, in FIGS. 10 and 16.

Figure 5:
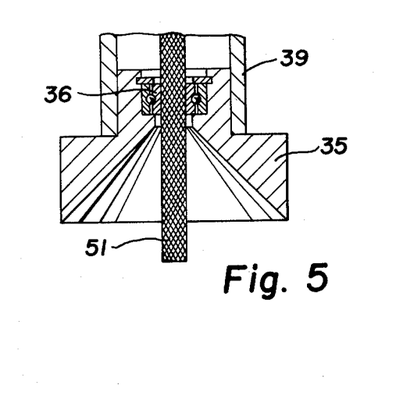
FIG. 5 is a fragmentary, sectional, detailed view of the rotary bearing of the drill guide assembly.

For convenience of description, reference will be made to the upper and lower ends of various components of the drill guide assembly and drill assembly, having reference to the orientation of FIG. 2. The drill guide assembly 30 includes a base shaft 31 having an offset handle 32 fixed to the upper end of the shaft to be grasped by the operator, and having an offset bracket 33 fixed to the lower end of the shaft and extending in the opposite direction. The offset bracket 33 is provided with an internally threaded hole at its end opposite from the shaft 31; and a guide sleeve 34 having an upper threaded end is threaded into the guide bracket hole and extends parallel to the shaft 31. A head 35 is mounted at the lower end of the guide sleeve; and this head is provided with a frusto-conical end face for centering the drill guide assembly on the prosthesis tip as will be described. As best seen in FIG. 5, the head 35 carries an anti-friction bearing 36 for centering the drill bit. A depth stop 37 in the form of a C-clamp is mounted on the shaft 31 and includes a clamping screw 38 for securing the depth stop at the desired elevation relative to the guide sleeve head 35. A depth gauge 39 consists of a rectangular block having a hole at one end by means of which it is slidably and rotatably mounted on the shaft 31 above the depth stop. The depth gauge has a selected thickness, ¼ inch for example, to control the depth of drilling as will be described.

Figures 3, 3A:
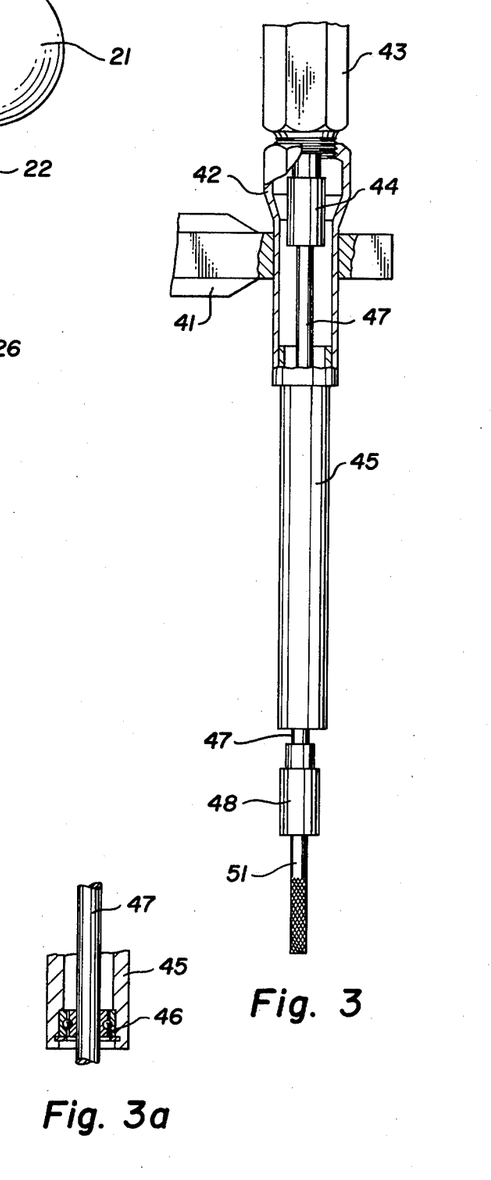
FIG. 3 is a fragmentary view, partially in section, showing details of the drill assembly.
FIG. 3A is a fragmentary, sectional, detailed view of the rotary bearing of the drill assembly.

The drill assembly 40 includes an elongated handle 41 to be gripped by the operator, the handle carrying a motor mount 42 adjacent to one end, the motor mount consisting of a tubular shank having a threaded box at its upper end, the axis of this motor mount being perpendicular to the length of the handle. A high speed pneumatic drill motor 43 includes a threaded pin at the lower end of the housing for engagement with the motor mount 42 and a drive shaft and associated drill bit chuck 44 extend from this end of the motor housing. A suitable drill motor is the Midas Rex Whirlwind Drill Motor, manufactured by Midas Rex Pneumatic Tool Company of Fort Worth, Tex., which drill motor has an output shaft capability of 73,000 rpm. A guide sleeve 45 is mounted concentrically with the motor mount 42 and extends downwardly from the handle 41. As best seen in FIGS. 3 and 3A, the lower end of the guide sleeve carries an anti-friction bearing 46 for rotationally guiding the lower end of a motor extension shaft 37 which carries a drill chuck 38 at its lower end. The extension shaft is inserted through the bearing at the lower end of the guide sleeve, and its upper end is secured in the motor chuck 44.

Figure 2:
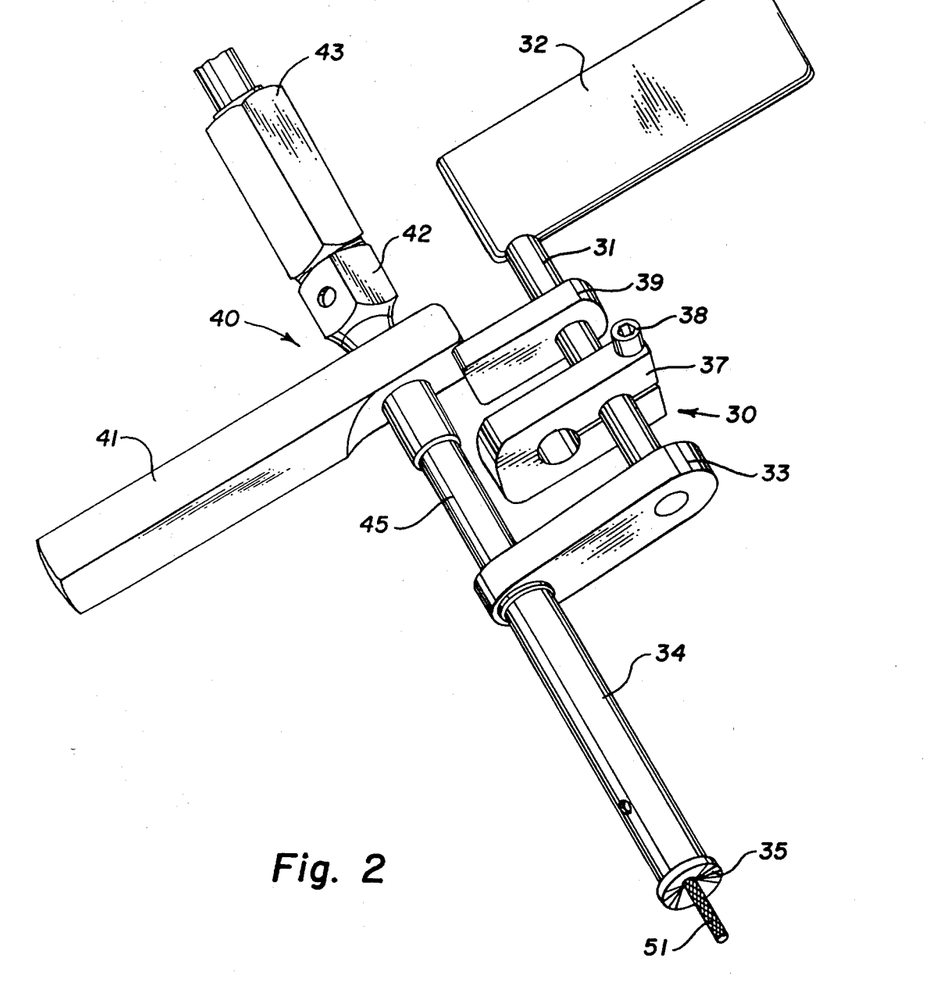
FIG. 2 is a perspective view showing the drill guide assembly and drill assembly in coacting relation.

FIGS. 2 and 3 illustrate a straight end cutting drill bit 51 used for the initial cutting to be described. The internal diameter of the guide sleeve 34 and the external diameter of the guide sleeve 45 are dimensioned that the latter sleeve will fit within the former with a relatively close sliding fit; and the guide sleeve bearing 36 is dimensioned to receive in close fitting relation the shank of the end cutting bit 51 which extends through this bearing and projects from the lower end of the guide sleeve 34.

Figure 4:
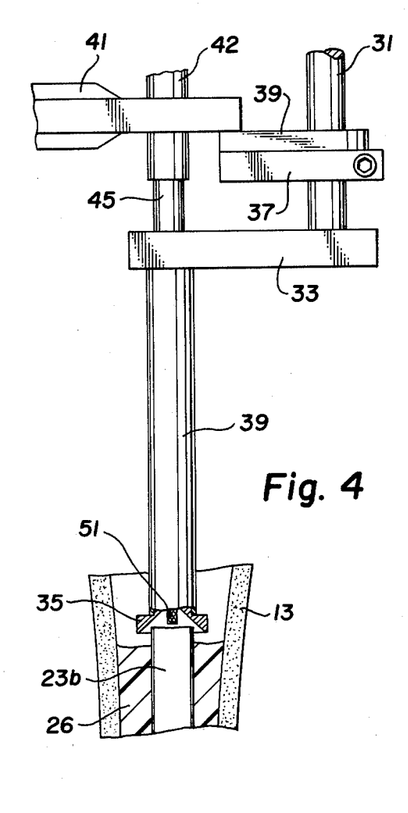
FIGS. 4 and 6 are fragmentary side views showing operational relationships of the drill guide assembly, drill assembly, and embedded prosthesis tip.
Figure 6:
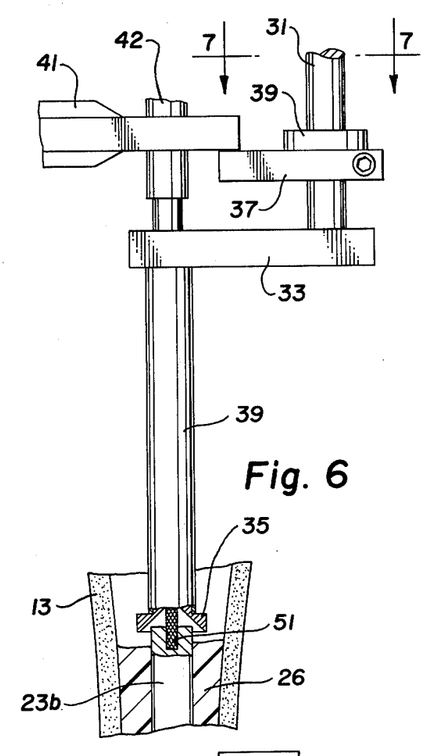

FIGS. 4 through 7 particularly illlustrate the relationships of the drill guide assembly 30 and drill assembly 40 to each other, and also to the fractured prosthesis tip 23b embedded within the femur 10 for the drilling of a generally axial hole into the exposed end of the tip. As seen in FIGS. 4 and 6, the surgical cement 26 has been removed from the intramedullary canal 14 to a depth somewhat below the fractured end face of the tip. This removal of the surgical cement might well be accomplished with the use of a suitable long, narrow cutting bit mounted directly in the motor chuck 44 of the above mentioned drill motor 43. The cement must be completely removed from around the upper end of the tip 23b so that the concave, frusto-conical end face of the drill guide head will fit over the tip end and seat firmly over the segment to prevent the drill guide and drill bit from wandering laterally once drilling begins. Ideally, the drill guide could be centered relative to the tip 23b so that the walls surrounding the drill hole will be sufficiently thick.

Figure 7:
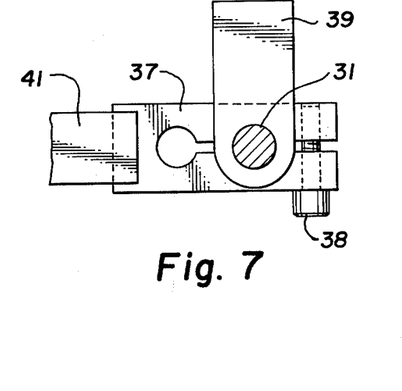
FIG. 7 is a fragmentary detailed view taken along the line 7—7 of FIG. 6.

FIG. 4 illustrates the setting up of the assemblies to begin drilling. The drill guide head 35 is located firmly relative to the prosthesis tip 23b, the depth stop 37 is released from clamping engagement with the shaft 31 to enable the drill assembly 40 to be moved downward to the point where the cutting end of the bit 51 just engages the fractured surface of the tip 23b. In this condition, the depth gauge 39 is placed in overlying relation to the depth stop 37, as seen in FIG. 4, and these two members are moved upwardly on the shaft 31, in interference relation with the handle 41 to the point where the upper face of the gauge 39 engages the lower face of the handle 41. The depth stop 37 is then clamped in this position on the shaft by means of the clamping screw 38. For the drilling operation the depth gauge 39 is moved out of interference position, as seen in FIGS. 6 and 7; and this allows the drilling of a hole to a depth determined by the interference engagement of the handle 41 with the stop 37. That completes the drilling of a generally axially aligned hole 27 of desired diameter and depth; and the drill guide assembly 30 is no longer needed.

Figure 8:
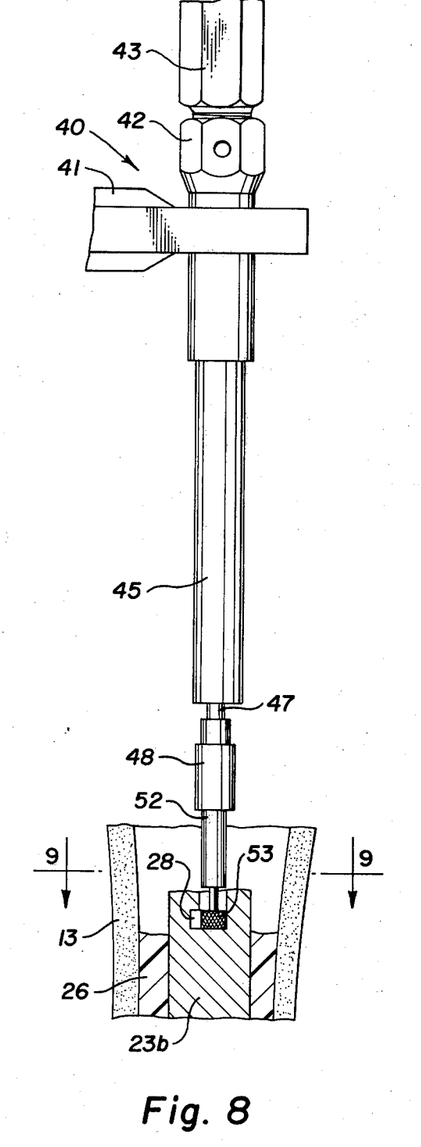
FIG. 8 is a side view of the drill assembly showing the undercutting drilling operation.
Figure 9:
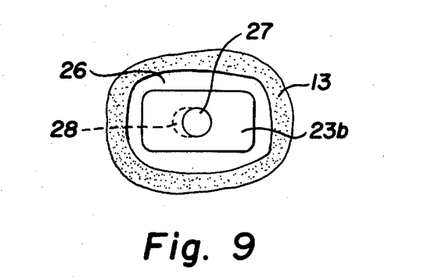
FIG. 9 is a detail view taken along the line 9—9 of FIG. 8.

The second drilling operation involves the cutting of an undercut recess 28 in the side wall of the hole 27 to provide a downward facing ledge. This operation is best illustrated in FIGS. 8 and 9; and for this operation an undercut drill bit 52 is mounted in the extension shaft chuck 48 of the drill assembly. The bit 52 has the same overall diameter as the straight bit 51; and is provided with a side cutting head 53 at its distal end joined to the remainder of the bit shank by a reduced diameter neck 54. This bit is inserted into the hole 27 and, with moderate side pressure on the drill assembly, the undercut recess 28 is formed at only one side of the hole as seen in the drawing.

Figure 14:
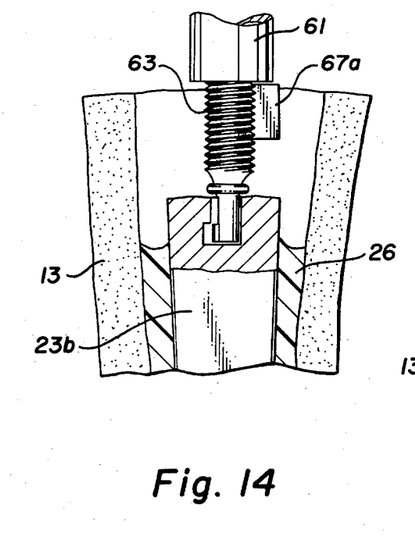
FIGS. 14 and 15 are detail views showing the operational relationship of the extractor and the hole formed in the prosthesis tip.
Figure 15:
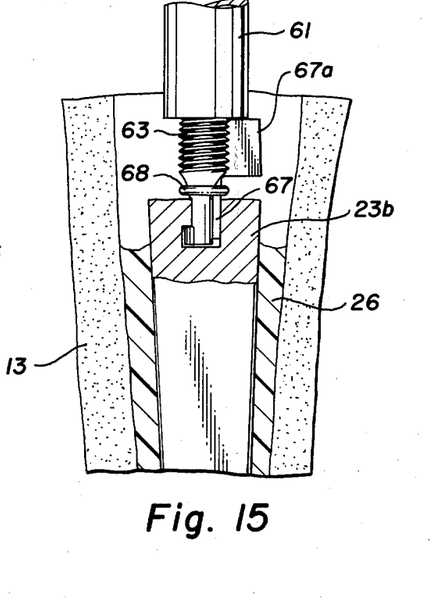

The remaining operations of the method are performed with the extractor assembly 60. One portion of this assembly, best seen in FIGS. 10 through 13, includes a cannulated T handle 61, an extractor 63, and an orienting wrench 70. The cannulated T handle consists of an elongated sleeve, internally threaded at both its upper and lower ends, and provided with transverse handles 62 projecting from its upper end to control rotation of the handle. The extractor 63 consists of an externally threaded body to be threadedly received within the lower threaded end of the T handle 61, and a downwardly projecting axial shaft 64 having a laterally projecting toe 65 at its distal end. The laterally projecting toe provides an upward facing ledge for coaction with the ledge provided by the undercut recess 28 in the prosthesis tip 23b. The shaft and toe are dimensioned to be received within the hole 27; and the shaft then is recessed along one face to define the toe 65 which projects to only one side of the shaft 64. An axially elongated cam slot 66 is provided in the face of the extractor 63, opposite from the toe 65, and this slot extends from a point adjacent to the distal end of the shaft 64 upward into the threaded body to a point adjacent to the top or proximal end of the body. The base of the slot lies generally in a plane parallel to the central axis of the extractor but is curved outwardly adjacent to the distal end. The follower wedge 67 is an enlongated member having a lower finger dimensioned to be received completely within the portion of the slot formed in the extractor shaft 64, when the parts are in the normal condition seen in FIG. 14, and includes a laterally projecting boss 67a adjacent to its upper end, which projects from the slot at the threaded portion of the body. When the extractor is threaded into the lower end of the cannulated handle 61, this boss is in interference relation with the lower end face of the cannulated handle, so that rotation of the handle relative to the extractor effects distalward movement of the follower wedge 67. With this distalward movement, the lower finger portion is cammed laterally outward relative to the extractor shaft to produce a wedging action. This wedging action is best seen with reference to FIGS. 14 and 15.

Prior to inserting this extractor assembly into the prosthesis hole 27, an orienting wrench 70 consisting of an elongated hex shank and a formed T handle 71 is inserted into the cannulated T handle 61 from the upper end thereof to be received in the hex recess 69 of the extractor. This orienting wrench is used to rotationally orient the extractor 63 relative to the hole so that the toe 65 is positioned to enter the recess 28. Maintaining this orientation by means of the orienting wrench 70, the T handle 61 is rotated effecting relative downward movement of the follower wedge to produce the wedging condition illustrated in FIG. 15 wherein the extractor toe is locked within the prosthesis recess 28, and wherein the respective ledges are placed in confronting relation.

Figure 16:
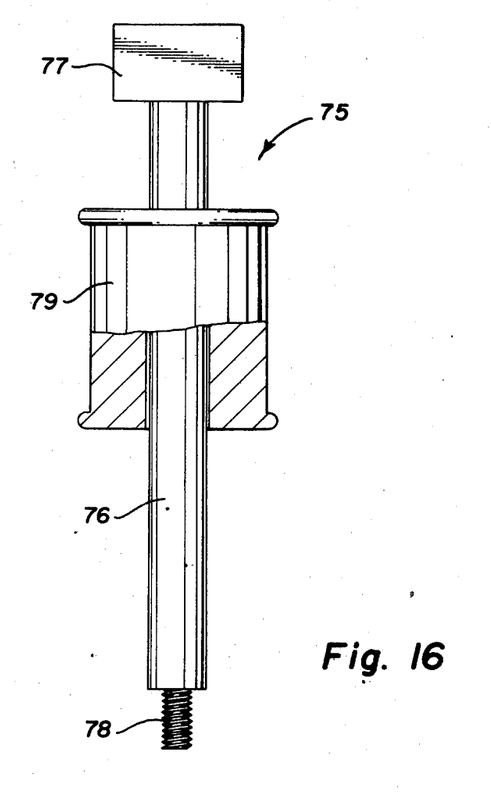
FIG. 16 is a side view of the impact hammer portion of the impact assembly.

To effect the withdrawal of the tip 23b from the femur, an impact hammer 75, is attached to the T handle 61. This impact hammer consists of an elongated shaft 76 having an integral enlarged head 77 at its upper end, and having a threaded pin 78 at its lower end. A hammer sleeve 79, of suitable mass, is slidably mounted over the shaft 76 to impact with the confronting face of the head 77. The threaded pin 78 is configured for mating threaded engagement with the internal threads at the upper end of the T handle 61. By means of gentle repetitive taps of the hammer sleeve against the head 77, the axial impact of blows transmitted to the prosthesis tip through the T handle and extractor effects the dislodgement of the tip. After removal of the tip, reverse rotation of the T handle relative to the extractor will effect the withdrawal of the follower wedge into the extractor by an O-ring 68; and enable separation of the extractor from the tip.

Method

The apparatus described above is one form of apparatus which may be used to practice the method of the invention; and the manner in which that apparatus is used to practice certain steps of the invention has been described. The following is an outline of method steps involved in withdrawing a prosthesis tip from a skeletal bone; and the method of the invention may include selected ones of these steps. After the upper end of the femur is displaced sufficiently from the mating hip bone, the upper end of the femoral component including the ball 20 is removed. This portion is probably loose to be withdrawn readily and, if not, may be readily driven out by suitable means. The surgical cement surrounding the removed portion of the stem 23b is then removed carefully to prevent any penetration or damage to the cortex 13 or head 11 of the femur. For this purpose the described pneumatic drill motor may be used with a suitable cutting tool. This surgical cement is removed around the prosthesis tip 23b to a point well below the surface 24 of the fracture to allow placement of a centerline drill guide over the exposed end of the embedded prosthesis tip. The drill guide sleeve provided with a suitably sized concave end face provides the functions of aligning the drill bit with the prosthesis tip, centering the drill bit with respect to the exposed end of the prosthesis tip, and preventing the lateral wandering of the drill bit during the drilling of the axial hole 27. This drilling step includes the limiting of the drilling to a preselected depth. An undercut is then formed to one side of the hole, spaced from the fracture surface, providing an inward facing ledge for engagement by an extractor tool. The tip is engaged by placing within the bore hole a shaft of an extractor tool dimensioned to be received within the bore hole, the shaft having a laterally projecting toe providing an axially inward facing ledge, with the toe configured to enter the undercut to place the respective ledges in confronting relation. The extractor shaft is wedged within the hole to maintain the respective ledges in that confronting relation. An impact tool is coupled to the extractor in axial alignment therewith so that gentle impact blows of the impact tool are transmitted through the extractor tool to the prosthesis tip to effect its withdrawal from the bone.

What has been described is a unique method for the extraction of the fractured tip of the femoral component of a total hip replacement, and unique apparatus for performing that method. A principal advantage of the technique described is that it eliminates the need for deliberately providing an aperture or window in the cortex of the femur, and also minimizes the possibility of an inadvertent penetration of the cortex. This substantially reduces the complications of revision surgery. An ancillary advantage is the elimination of the need for a long-stem component for the revision prosthesis, and the attendant complications which accompany the implant of that component, and which would result should future revision surgery again be required.

A further advantage of the described technique is that it is suitable for use with extremely hard, so-called space-age metals, thereby enabling the extraction of fractured prosthesis tips made from such metals, where such extraction might otherwise be extremely difficult.

While preferred embodiments of the invention have been illustrated and described, it will be understood by those skilled in the art that changes and modifications may be resorted to without departing from the spirit and scope of the invention.

What is claimed is:

1. Apparatus for removing a fragment of a prosthesis from embedment in a bone, comprising a drill assembly including an elongated tubular support, a drill motor mounted at one end of said tubular support having a drive shaft extending therethrough, and drill chuck means mounted at the end of said shaft projecting from said support;

a drill guide assembly including an elongated tubular drill guide dimensioned to receive said tubular support in sliding relation, one end of said drill guide having a recessed end face configured to overlie and engage an end of the prosthesis, and means for limiting movement of said drill assembly relative to said drill guide end face;

drill bit means for drilling a hole with an undercut ledge in the prosthesis;

an extractor assembly including an extractor having an externally threaded body and an internally threaded tubular holder for said body; said extractor having an axial shaft to be received in said hole, said shaft having laterally projecting means at its distal end defining a ledge; said extractor having a longitudinal cam slot for guiding a follower wedge, said follower wedge being movable axially by the end face of said tubular holder to effect lateral movement of said shaft within said hole to place said ledges in interference relation;

and said extractor assembly further including means for coupling to said extractor holder for imparting axial impact blows to said extractor.

2. Apparatus as set forth in claim 1
said drill assembly including an elongated tubular support, a drill motor mounted at one end of said tubular support having a drive shaft extending therethrough, bearing means in said tubular support for rotationally supporting said drive shaft; drill chuck means mounted at the end of said shaft projecting from said support; and handle means mounted in said drill support to enable independent manual manipulation and guidance thereof;

said drill guide assembly including an elongated tubular drill guide dimensioned to receive and guide said tubular support for relative axial and rotational movement, one end of said drill guide having a recessed end face configured to locate said one end relative to an end of said fragment, handle means mounted on said tubular drill guide to enable manual manipulation and guidance thereof; and means for limiting axial movement of said drill assembly relative to said drill guide assembly.

3. Apparatus as set forth in claim 2
said drill guide assembly including bearing means disposed in the lower end of said tubular drill guide for rotationally supporting a drill bit mounted in said drill chuck means.

4. Apparatus as set forth in claim 2
said drill guide assembly including a support shaft mounted in parallel offset relation with said tubular drill guide; a stop member mounted in sliding relation on said support shaft and disposed for interfering relation with said drill assembly, said stop member having clamp means for securing said member in selected position on said shaft;

a depth gauge rotatably mounted on said shaft and disposed for overlying relation with said stop member and interfering relation with said drill assembly.

5. Apparatus as set forth in claim 2 said drill assembly handle means comprising a member extending laterally from said elongated drill support;

said drill guide assembly handle means comprising a member extending laterally from said support shaft.

6. Apparatus as set forth in claim 2
said drill guide assembly including an adjustable stop member mounted for movement parallel to the longitudinal axis of said tubular drill guide and disposed for interfering relation with said drill assembly, said stop member having means for securing said member in a selected position;

a depth gauge mounted in overlying relation with said stop member, being movable relative to said stop member for selective interfering and non-interfering relation with said drill assembly.

7. Apparatus as set forth in claim 1
said longitudinal cam slot extending along said extractor shaft;

said follower wedge being movable axially along said cam slot, by said tubular holder, to effect the camming of said wedge laterally out of said slot within said hole and thereby shift said shaft laterally to place said ledges in said interference relation.

8. Apparatus as set forth in claim 1
said extractor body having a socket recess in its inner end; said extractor assembly including an orienting wrench having an elongated shaft to extend through said tubular holder for engagement with said socket recess; and said tubular holder having handle means for rotation thereof relative to said extractor and said orienting wrench.

9. Apparatus as set forth in claim 1
said cam slot having a base including a linear portion disposed parallel to the axis of said extractor shaft, and including a top portion curving outwardly from the linear portion adjacent to the distal end of said shaft; said follower wedge having an axially extending finger configured to be received within the linear portion of said cam slot, in a retracted condition of said follower wedge; and said follower finger being cammed laterally outward by said curved tip portion of said cam slot in response to distalward movement of said follower wedge urged by said tubular holder.

10. Apparatus as set forth in claim 1
resilient band means surrounding said extractor shaft and said follower wedge, for urging said follower wedge to its retracted condition within said cam slot.

11. In apparatus for removing a fragment of a prosthesis from embedment in a bone, wherein a hole with an undercut ledge has been formed in one end of the prosthesis an extractor assembly including an extractor having an externally threaded body and an internally threaded tubular holder for said body; said extractor having an axial shaft to be received in said hole, said shaft having laterally projecting means at its distal end defining a transverse ledge; said extractor having a longitudinal cam slot extending along said shaft for guiding a follower wedge, said follower wedge being engageable and movable axially by the end face of said tubular holder to effect the camming of said wedge laterally out of said slot within said hole to place said ledges in interference relation;

and said extractor assembly further including means for coupling to said extractor holder for imparting axial impact blows to said extractor.

12. Apparatus as set forth in claim 11 said extractor body having a socket recess in its inner end;

said extractor assembly including an orienting wrench having an elongated shaft to extend through said tubular holder for engagement with said socket recess; and said tubular holder having handle means for rotation thereof relative to said extractor and said orienting wrench.

13. Apparatus as set forth in claim 11 said cam slot having a linear base parallel to the axis of said extractor shaft, and the base curving outwardly adjacent to the distal end; said follower wedge having an axially extending finger disposed within the cam slot in said extractor shaft in retracted condition; and said follower finger being cammed laterally outward in response to distalward movement of said follower wedge in said cam slot.

14. Apparatus as set forth in claim 13 said follower wedge having a laterally projecting boss for engagement by the end face of said tubular holder.

15. Apparatus as set forth in claim 11 said means for imparting axial impact blows comprising a slide hammer including an elongated shaft having an integral head at one end, and having means at its other end for coupling to said tubular holder, and a sliding mass disposed over said shaft for impact engagement with said integral head.

16. A method for removing a fragment of a fractured elongated prosthesis from embedment in a bone comprising the steps exposing one end of said fragment;

forming a hole in said one end of said fragment, aligned generally axially with the long dimension of the prosthesis;

forming an undercut ledge in the wall of said hole spaced from the entrance thereof;

placing in said hole an extractor shaft having a laterally projecting toe providing a transverse ledge;

wedging said extractor shaft laterally within said hole to urge said toe ledge into axially interfering relation with said undercut ledge;

and imparting impact blows to said extractor shaft, along the axis thereof, for transmission to said fragment through said interfering ledges, and thereby removing said fragment from embedment in said bone.

17. A method as set forth in claim 16 including the step removing surgical cement from the space around the exposed end of said prosthesis.

18. A method as set forth in claim 16 including the step placing a locating end face of an elongated drill guide in engagement with the exposed end of the prosthesis, with the drill guide in general axial alignment therewith, to guide a drill forming said hole.

19. A method as set forth in claim 16 including the step providing said extractor shaft with an axially elongated cam slot, and with a follower wedge guided for axial movement in said slot;

displacing said follower wedge axially in said slot to effect coincident lateral displacement of said follower wedge by said cam slit, thereby to wedge said extractor shaft to one side of said hole to place said ledges in said interfering relation.

20. A method as set forth in claim 19 including the step providing said extractor shaft with axial threads, coupling to said extractor shaft by means of said threads, a threaded actuator shaft;

threading said actuator shaft relative to said extractor to effect said axial displacement of said follower wedge.

21. A method as set forth in claim 20 including the step coupling an impact hammer to said actuator shaft for imparting and transmitting said impact blows to said extractor shaft through said actuator shaft.

22. A method as set forth in claim 16 including the step coupling an impact tool to said extractor shaft for imparting said impact blows.

* * * * *

UNITED STATES PATENT AND TRADEMARK OFFICE
CERTIFICATE OF CORRECTION

PATENT NO. : 4,399,813

DATED : August 23, 1983

INVENTOR(S) : Forest C. Barber

It is certified that error appears in the above-identified patent and that said Letters Patent is hereby corrected as shown below:

Column 1, line 41, "siz" should read -- size --.

Column 4, line 34, "distal" should read -- proximal --.

Column 12, Claim 20, line 34, after "extractor" insert -- shaft --.

Signed and Sealed this

Sixth Day of January, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,399,813

DATED : August 23, 1983

INVENTOR(S) : Forest C. Barber

It is certified that error appears in the above-identified patent and that said Letters Patent are hereby corrected as shown below:

Column 1, line 41     change "siz" to --size--;
Column 4, line 34     change "distal" to --proximal--;
Claim 17, line 12     change "prosthesis" to --fragment--;
Claim 18, line 16 &
         line 17     change "the prosthesis" to --said fragment--;
Claim 20, line 34     after "extractor" insert --shaft--.

This certificate of correction supersede certificate issued Jan. 6, 1987.

Signed and Sealed this

Tenth Day of February, 1987

Attest:

DONALD J. QUIGG

Attesting Officer       Commissioner of Patents and Trademarks